(12) United States Patent
Skyba et al.

(10) Patent No.: US 7,347,821 B2
(45) Date of Patent: Mar. 25, 2008

(54) ADAPTIVE PROCESSING OF CONTRAST ENHANCED ULTRASONIC DIAGNOSTIC IMAGES

(75) Inventors: Daniel Skyba, Bothell, WA (US); Damien Dolimier, Salem, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 615 days.

(21) Appl. No.: 10/872,843

(22) Filed: Jun. 21, 2004

(65) Prior Publication Data

US 2004/0267125 A1    Dec. 30, 2004

Related U.S. Application Data

(60) Provisional application No. 60/482,657, filed on Jun. 26, 2003.

(51) Int. Cl.
*A61B 8/00* (2006.01)
(52) U.S. Cl. .......................... 600/443; 128/916
(58) Field of Classification Search ................ 600/437, 600/443–447, 454–456, 458; 128/916; 382/128
See application file for complete search history.

(56) References Cited

U.S. PATENT DOCUMENTS

| | | | |
|---|---|---|---|
| 5,309,914 A | 5/1994 | Iinuma | |
| 5,360,006 A | 11/1994 | Geiser et al. | |
| 5,457,754 A | 10/1995 | Han et al. | |
| 5,458,126 A | 10/1995 | Cline et al. | |
| 5,465,721 A * | 11/1995 | Kishimoto et al. | 600/443 |
| 5,538,003 A | 7/1996 | Gadonniex et al. | |
| 5,579,768 A * | 12/1996 | Klesenski | 600/442 |
| 5,669,382 A * | 9/1997 | Curwen et al. | 600/425 |
| 5,971,924 A | 10/1999 | Ochi | |
| 6,106,465 A | 8/2000 | Napolitano et al. | |
| 6,106,466 A | 8/2000 | Sheehan et al. | |
| 6,213,951 B1 | 4/2001 | Krishnan et al. | |
| 6,491,636 B2 * | 12/2002 | Chenal et al. | 600/450 |
| 6,708,055 B2 * | 3/2004 | Geiser et al. | 600/425 |

\* cited by examiner

Primary Examiner—Francis J. Jaworski (57) ABSTRACT

A method is described for automatically and accurately defining tissue borders within ultrasound imaging. A preferred embodiment described provides for accurately delineating endocardial and epicardial tissue borders during ultrasound imaging of the heart using contrast agents. The inventive method requires first defining a set of threshold values corresponding to various imaging depths and correlated within the image. The invention further uses the set of threshold values and a maximization function to accurately identify the tissue boundaries.

40 Claims, 11 Drawing Sheets

FIG. 1

PRIOR ART

ADAPTIVE PROCESSING OF CONTRAST ENHANCED ULTRASONIC DIAGNOSTIC IMAGES

CROSS REFERENCE TO RELATED CASES

Applicants claim the benefit of Provisional Application Ser. No. 60/482,657, filed Jun. 26, 2003.

BACKGROUND OF THE INVENTION

This invention relates to ultrasonic diagnostic imaging systems and, in particular, to ultrasonic diagnostic imaging systems, which utilize adaptive processing of contrast-enhanced ultrasound images to accurately and/or automatically detect and define tissue boundaries.

Conventional ultrasound diagnostic imaging procedures, which quantify bodily structures and functions, rely upon an assumption that the acquired ultrasound data will clearly delineate and define tissue boundaries. When the quantification or measurement procedure uses static images or a small set of measurements, the delineation of the bodily structure may be measured manually. An example of such a procedure is the obstetrical measurements of a developing fetus. The static images of the developing fetus must be acquired during periods when fetal activity is low. Once an image is acquired, only a few circumference or length measurements are usually required to compute development characteristics such as gestational age and anticipated delivery date from the static images. These measurements can readily be made manually on the fetal images. Manual measurements, however, may be time consuming and subjective.

Other diagnostic imaging procedures, particularly those involving movement in and/or around the object being imaged, for example, taking measurements of the heart and its functioning (e.g., ejection fraction), are much more complicated than simply measuring static images. The heart is always beating and hence tissue and blood are always in motion. More particularly, as the heart contracts and expands (relaxes) to pump blood, its contours (endocardial and epicardial boundaries) constantly move and change with respect to image space. To fully assess many characteristics of cardiac function, it is necessary to evaluate many, and at times all, of the images acquired during the heart cycle (one heartbeat). This may amount to thirty to one hundred and fifty or more images. Cardiac structures of interest, such as the endocardium, epicardium or valves, must then be delineated in each of the images. The constant cardiac motion causes the structures to appear slightly different in each image or frame acquired during the cardiac cycle. This is a painstaking, time-consuming task for a technician. And while ultrasonic contrast agent injected into the blood provides for delineating between myocardium and vascular pathways, contrast agent is nevertheless a strong attenuator of ultrasound energy, which under certain circumstances leads to blurring of tissue boundaries and inaccurate interpretation of cardiac function.

The state of the art of ultrasound imaging and diagnosis, including but not limited to cardiac and vascular imaging and diagnostics, would readily benefit from an improved and/or automatic process for more clearly delineating specific anatomy and tissue boundaries. Quantification of cardiac function often relies on the delineation of structure or tissue boundaries as an input. For example, myocardial wall thickening is currently assessed in stress-echocardiographic exams, where, for example, the actual size of the ventricle is measured and diagnosis is based on such measurement. The degree of wall thickening is typically qualitatively scored by the clinician conducting the stress test without the use of measurement tools because (as mentioned above) segmental measurements over the cardiac cycle are too time-consuming. This leads to inaccuracies and misdiagnosis. Moreover, techniques for assessing blood perfusion information using contrast agents or Doppler techniques which rely upon conventional processes and techniques for delineating cardiac borders are also inaccurate at times.

Research into systems that automatically analyze ultrasound images and draw borders around objects in the images has been underway for over a decade. Progress is at times impeded by the inherent specular nature of and speckle noise within ultrasound images, as well as the variability with which tissue structures may appear in an image. Many conventional systems use assisted or semi-automatic approaches, which require that the user manually mark key reference points in an image, or draw a complete border of an object in one image. The inputs are then used as references from which the balance of a border or other borders will be drawn. This need for user input limits semi-automatic techniques to operating only with stored images and prevents their use in real time.

Several prior art writings which may provide a flavor of the issues involved in ultrasound imaging of cardiac borders include Wilson, et al., Automated Vessel Analysis Of Echocardiographic Apical 4-Chamber Images; DEPT. OF MATHMATICS, UNIVERSITY OF FLORIDA, Gainesville, Fla. 32611, SPIE, August, 2000; Hozumi, et al., Echocardiographic Estimation Of Left Ventricular Cavity Area With a Newly Developed Automated Contour Tracking Method, American Society of Echocardiography, October 1997, pgs. 822-829; Mignotte, et al., Endocardial Boundary Estimation And Tracking In Echocardiographic Images Using Deformable Templates And Markov Random Fields, Pattern Analysis & Applications (2001), 4:256-271.

An automatic border detection (ABD) system which reliably delineates the border of an object in an ultrasound image without user preconditioning, and in real time is found in U.S. patent application Ser. No. 09/732,613. The application is commonly owned with the owner hereof, and its disclosure is incorporated herein by reference in its entirety. The inventive content shall be referred to hereinafter as "Philips ABD inventions." The Philips ABD inventions teach techniques for automatically, and with user input, delineating the border or boundary of an object by locating key landmarks of the ultrasound image of the object. After locating the key landmarks in the ultrasound image data, the inventive processes fit one of a plurality of predefined standard shapes to the landmarks and object. In one particular embodiment of the Philips ABD inventions, an ultrasound system is disclosed which displays both the end systole and end diastole images of a cardiac cycle, and automatically draws borders on both images.

Figure 1:
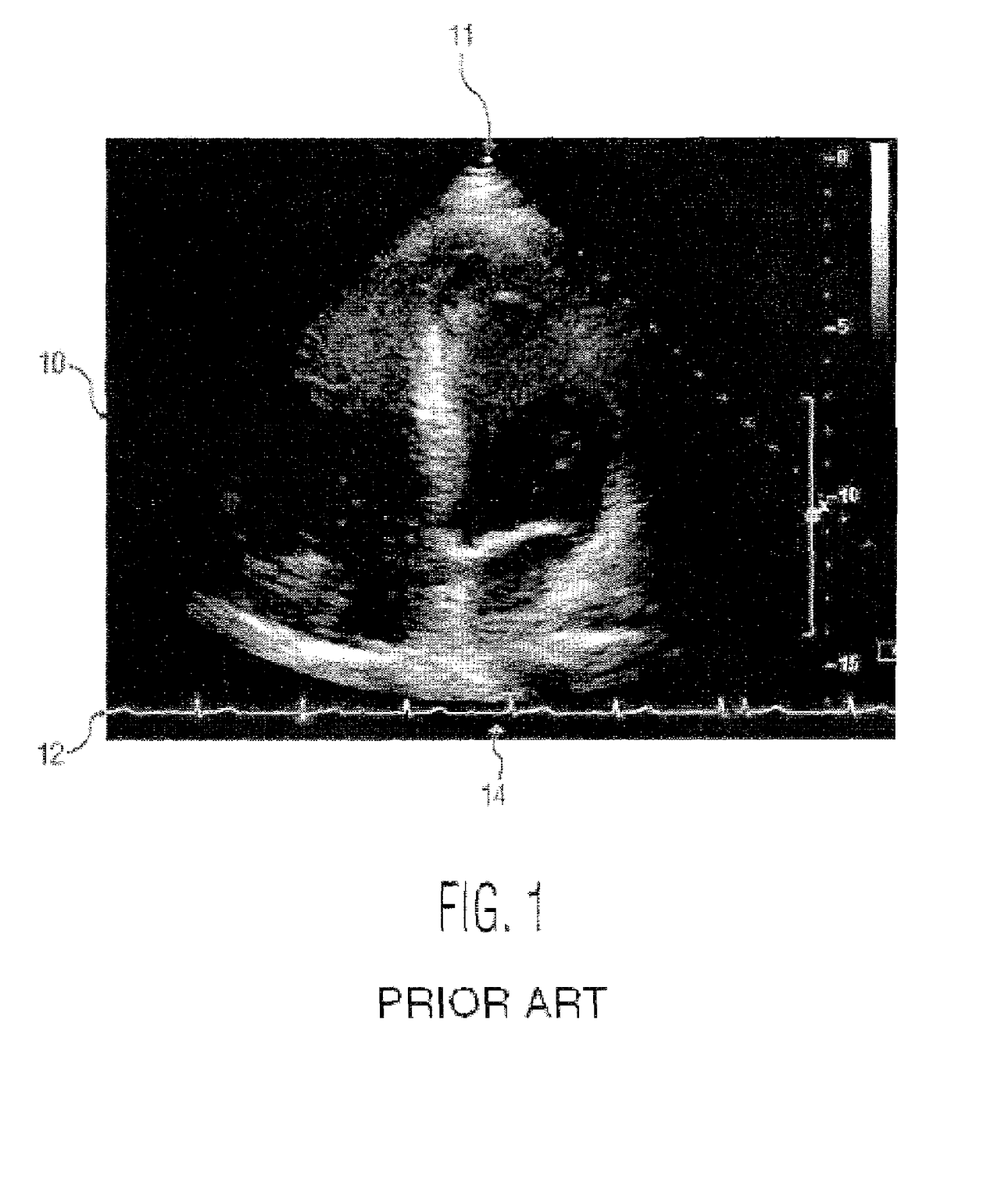
FIG. 1 is a prior art illustration of a four-chamber ultrasound image of the heart.

Prior art FIG. 1 herein corresponds to the Philips ABD inventions. More particularly, FIG. 1 shows an ultrasound image 10 which is one of a sequence of an apical four-chamber view of the heart, which was acquired by a phased array transducer probe. The prior art acquisition process requires that the probe is oriented to view the heart from the proximity of its apex 11. The largest chamber in the image (the central and upper right portion of the image) is the left ventricle (LV). As the real-time ultrasound image sequence is acquired, an ECG trace 12 of the heart cycle is simultaneously acquired and displayed at the bottom of the display.

Triangular marker 14 denotes the point or phase of the cardiac cycle at which the currently displayed image was acquired.

As the user views the display of FIG. 1, the heart is seen beating in real time as the ECG waveform 12 scrolls beneath the ultrasound images 10. The instantaneously displayed heart phase is indicated by the marker 14. A typical duration of the heart cycle when the body is at rest is about one second. Imaging of one cycle consequently requires acquiring and displaying approximately 30-90 image frames. Clinicians often acquire and save the sequence of images of a heart cycle and then replay them (in a continuous "loop"), repetitively displaying the selected cardiac cycle.

Figure 2:
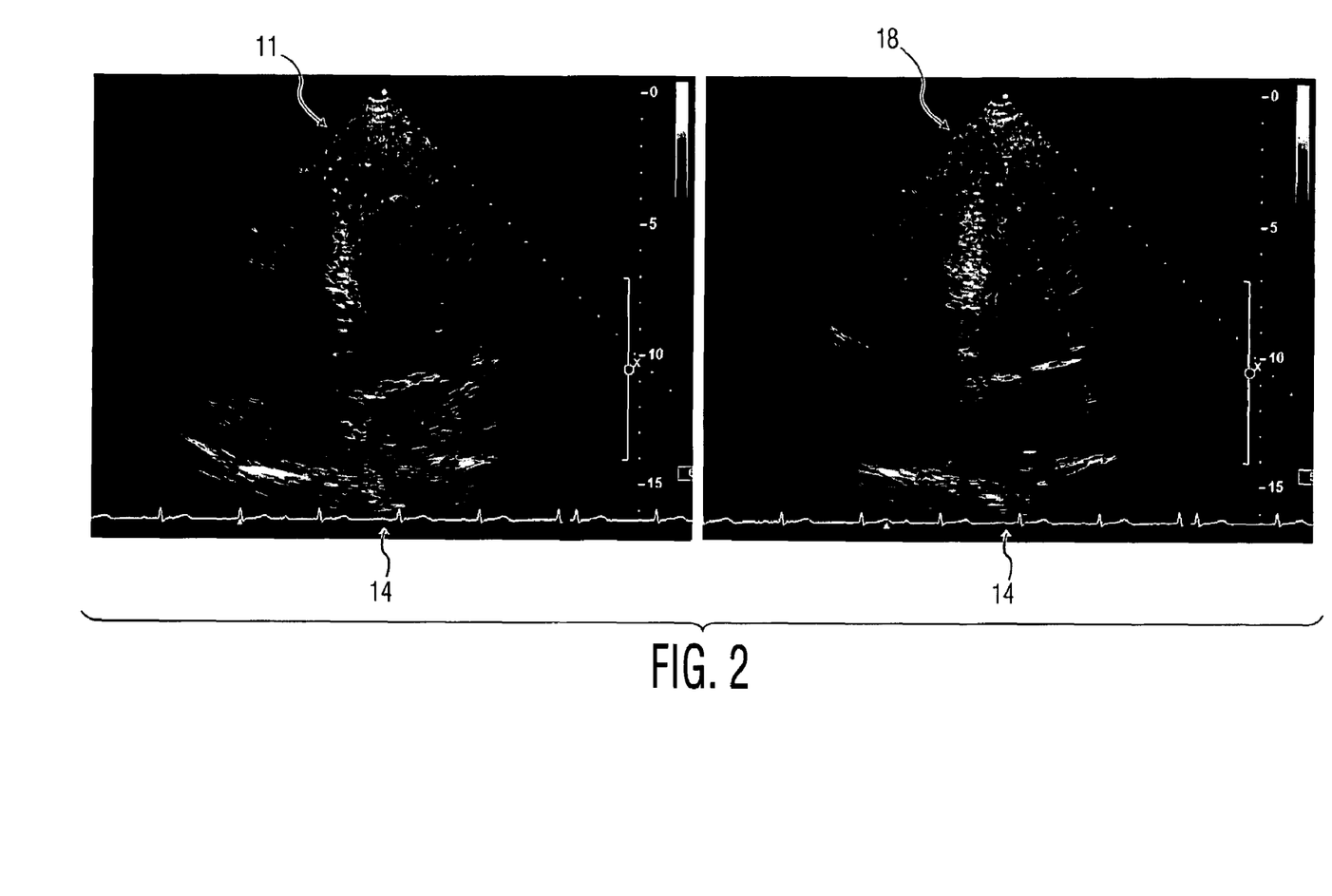
FIG. 2 is a prior art illustration of an ultrasound display of both end diastole and end systole cardiac images.

When the protocol of the FIG. 1 embodiment of the Philips ABD inventions is actuated, the display changes to a dual display. The process is highlighted in prior art FIG. 2, where an end diastole image 16, and end systole image 18 are displayed side-by-side. The protocol also recognizes the end diastole and end systole points of the cardiac cycle in relation to the R-wave of the ECG waveform 12. That is, the ECG waveform R-wave is used to identify and display the ultrasound images at these two phases of the heart cycle. The dual display of prior art FIG. 2 shows the ECG waveform 12 for the selected heart cycle beneath each ultrasound image. Marker 14 indicates the end diastole and end systole phases at which the two displayed images were acquired.

Figure 3A:
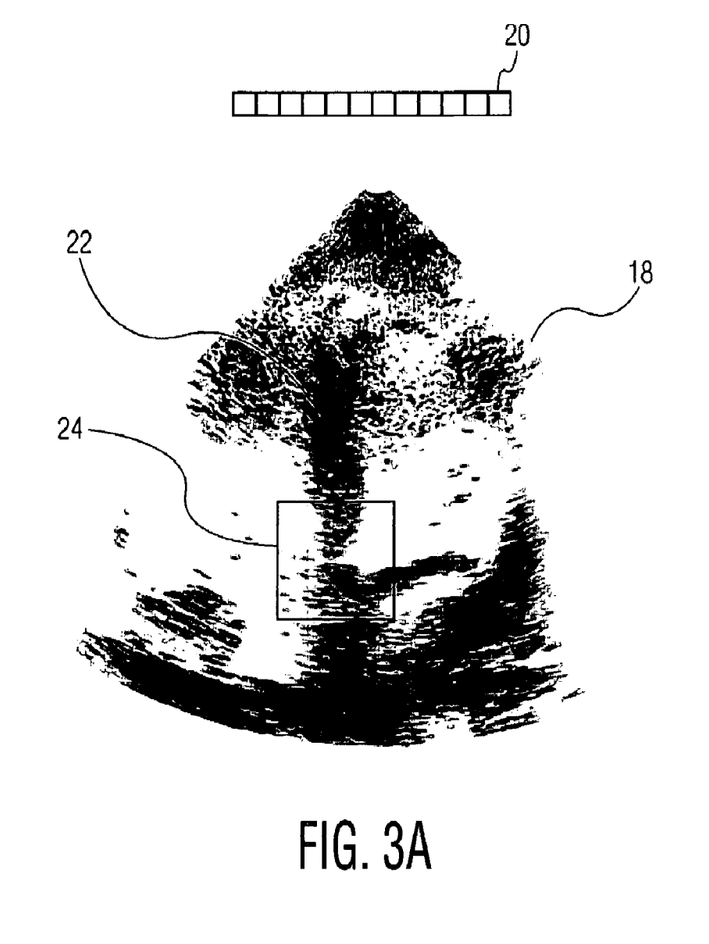
FIGS. 3A and 3B are illustrations which depict a step within a prior art automatic edge detection process which includes locating the medial mitral annulus (MMA) and lateral mitral annulus (LMA) in an ultrasound image of the left ventricle (LV)

The protocol further provides that the ABD-driven processor first draws the endocardial border of the LV in the end systole image 18 of prior art FIG. 3A. The first step in drawing the border of the LV requires locating three key landmarks in the image, the medial mitral annulus (MMA), the lateral mitral annulus (LMA), and the endocardial apex. Defining a search area 24 for the MMA (as shown in FIG. 3A) begins the process of locating. The ABD-driven processor is preconditioned to analyze four-chamber views of the heart with the transducer 20 from its apex. Consequently, it expects the brightest vertical near field structure in the center of the image to be the septum 22. This means that the column of pixels in the image with the greatest total brightness value should define the septum. With these cues, the prior art ABD-driven processor locates the septum 22, and then defines an area in which the MMA should be identified. This area is defined from empirical knowledge of the approximate depth of the mitral valve from the transducer in an apical view of the heart. Search area 24 is defined in this manner.

Figure 4A:
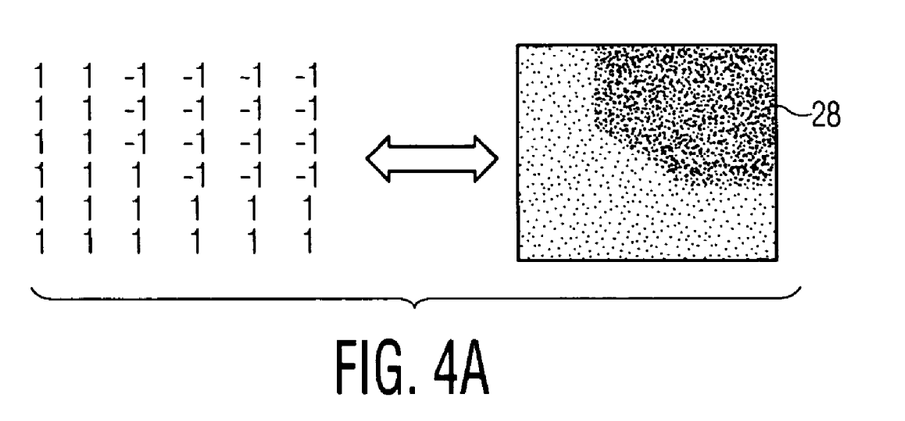
FIGS. 4A and 4B, are prior art illustrations depicting geometric templates used to locate the MMA and LMA in the prior art process described.

A filter template defining the anticipated shape of the MMA is then cross-correlated to the pixels in the MMA search area. This template may be created from expert knowledge of the appearance of the MMA in other four-chamber images as used by Wilson, et al., in their paper "Automated analysis of echocardiographic apical 4-chamber images," *Proc. of SPIE,* August, 2000. For that matter, it appears that any of a geometric corner template, right angle corner template, and octagon corner template may be used as filter templates. For example, an octagon corner template 28 (the lower left corner of an octagon) as their search template for the MMA is shown at the right side of prior art FIG. 4A, where in actual practice, the binary matrix shown at the left side of prior art FIG. 4A represents the octagon template.

The conventional ABD-driven processor performs template matching by cross-correlating different sizes of this template with the pixel data in different translations and rotations until a maximum correlation coefficient above a predetermined threshold is found. To speed up the correlation process, the template matching may initially be performed on a reduced resolution form of the image. This highlights major structures and may be produced by decimating the original image resolution. When an initial match of the template is found, the resolution may be progressively restored to its original quality and the location of the MMA progressively refined by template matching at each resolution level. Once the MMA has been located, a similar search is made for the location of the LMA, as shown in prior art FIG. 3B.

Figure 3B:
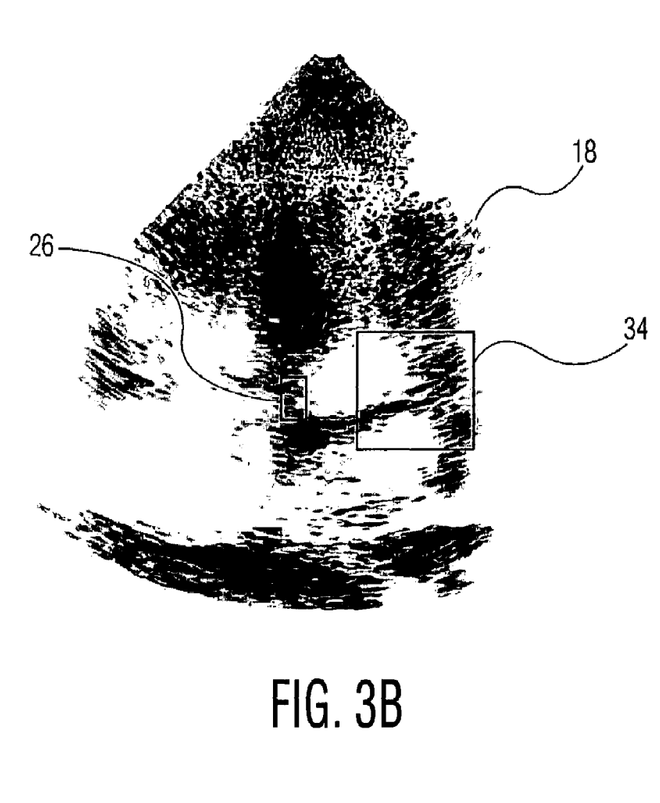
Figure 4B:
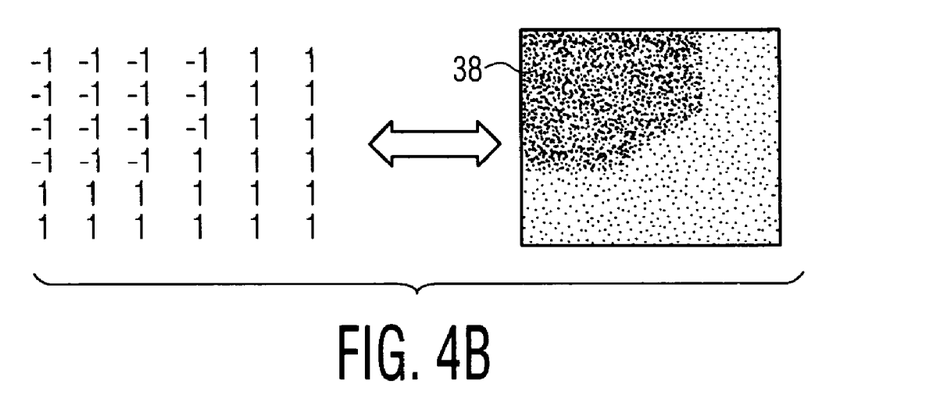

In prior art FIG. 3B, a small box 26 marks the location established for the MMA in the image 18, and a search area to the right of the MMA is defined as indicated by a box 34. A right corner geometric template, preferably a right octagon corner template 38 as shown in prior art FIG. 4B, is matched by cross-correlation to the pixel values in the search area of box 34. Again, the image resolution may be decimated to speed the computational process and different template sizes may be used. The maximal correlation coefficient exceeding a predetermined threshold defines the location of the LMA. With the MMA 26 and the LMA 36 found, the next step in the process is to determine the position of the endocardial apex, which may be determined as shown in prior art FIG. 5.

Figure 5:
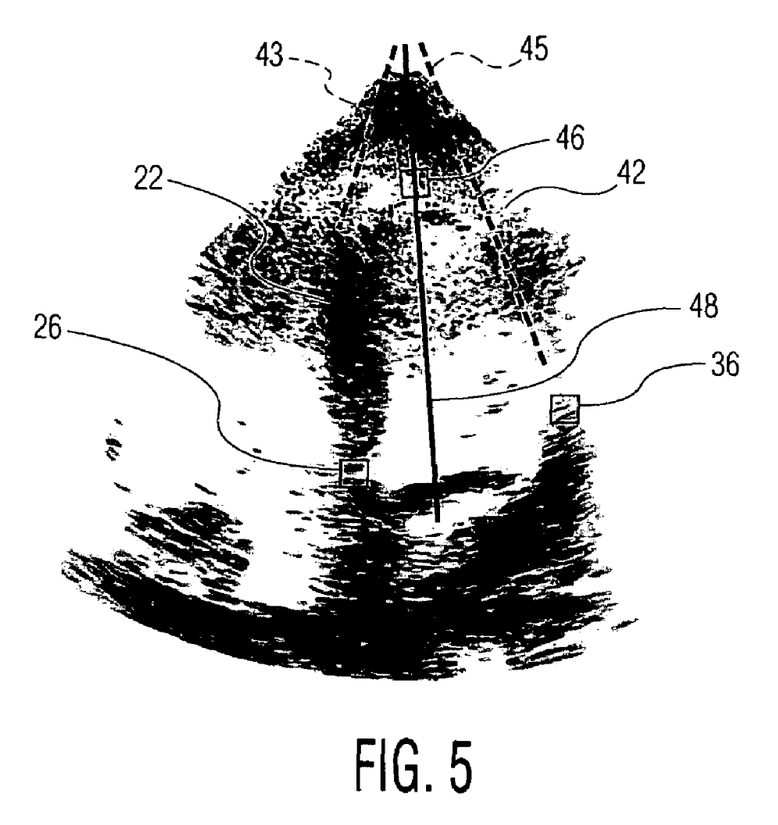
FIG. 5 is an illustration depicting at step of locating the apex of the LV.

The pixel values of the upper half of the septum 22 are analyzed to identify the nominal angle of the upper half of the septum, as indicated by the broken line 43. The pixel values of the lateral wall 42 of the LV are analyzed to identify the nominal angle of the upper half of the lateral wall 42, as shown by the broken line 45. If the lateral wall angle cannot be found with confidence, the angle of the scanlines on the right side of the sector is used. A line 48 bisects the angle between the broken lines 43, 45, and the apex is initially assumed to be located at some point on this line. With the horizontal coordinate of the apex defined by line 48, a search is made of the slope of pixel intensity changes along the line 48 to determine the vertical coordinate of the apex. This search is made over a portion of line 48 which is at least a minimum depth and not greater than a maximum depth from the transducer probe, approximately the upper one-quarter of the length of line 48 above the mitral valve plane between the MMA 26 and the LMA 36. Lines of pixels along the line 48 and parallel thereto are examined to find the maximum positive brightness gradient from the LV chamber (where there are substantially no specular reflectors) to the heart wall (where many reflectors are located).

Figure 6A:
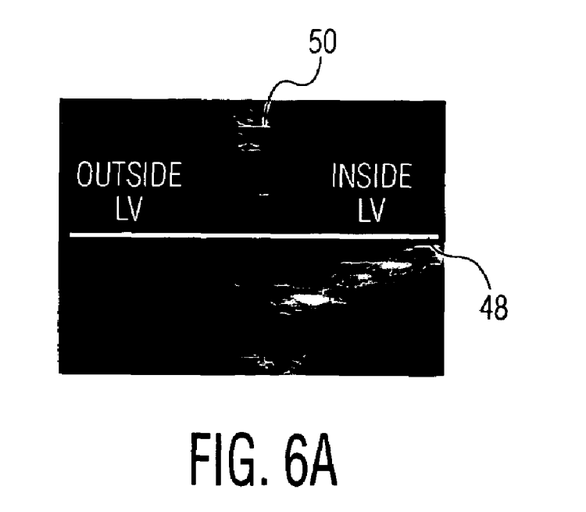
FIGS. 6A, 6B, 6C are illustrations depicting a prior art technique for fitting a standard border shape to the endocardial boundary of the LV.
Figure 6B:
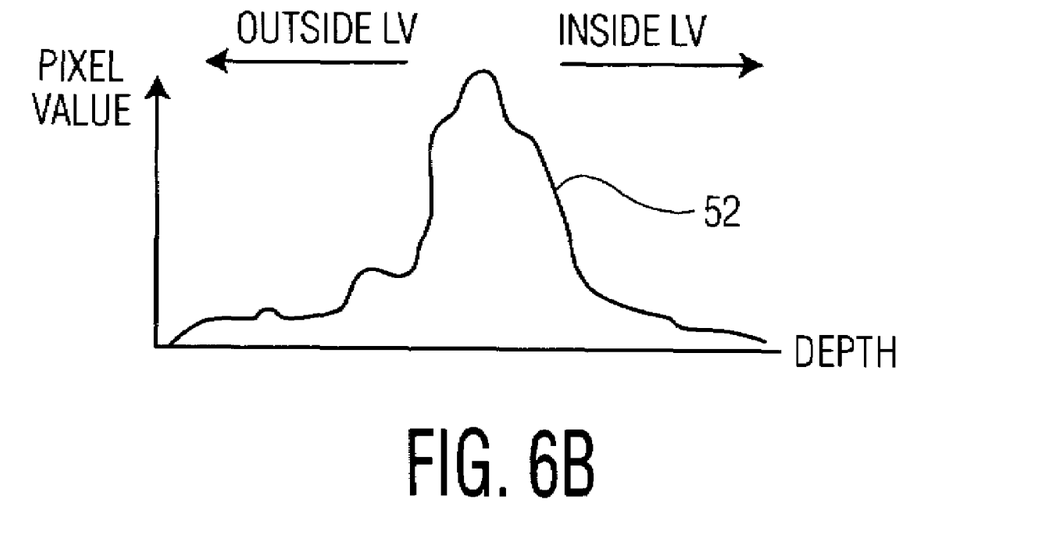
Figure 6C:
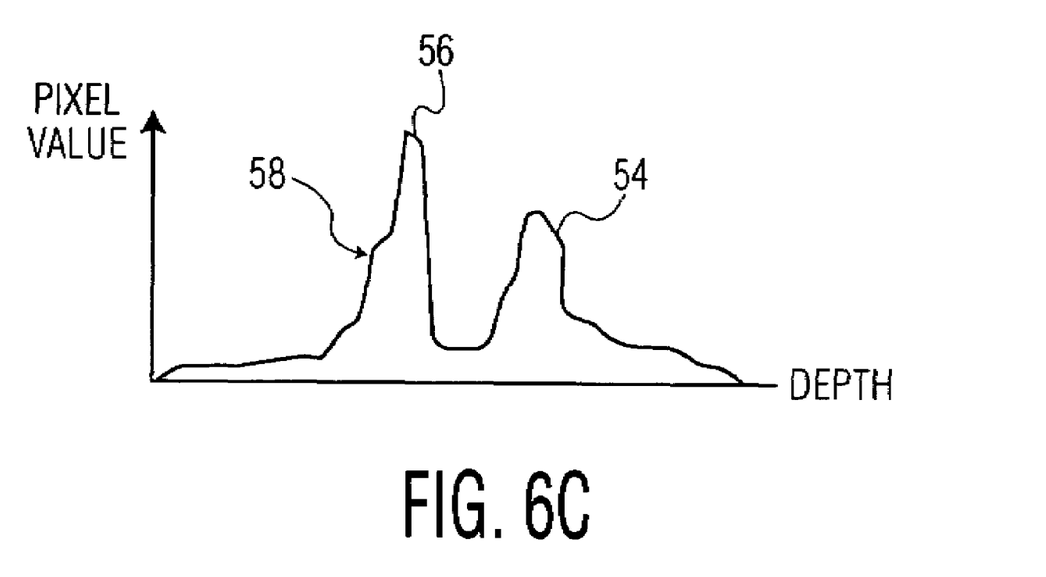

A process for finding a gradient is part of Philips ABD inventions, which may be understood broadly by viewing prior art FIGS. 6A, 6B, and 6C. More particularly, FIG. 6A shows a portion of an ultrasound image including a section of the heart wall 50 represented by the brighter pixels in the image. Drawn normal to the heart wall 50 is a line 48, which, from right to left, extends from the chamber of the LV into and through the heart wall 50. If the pixel values along line 48 are plotted graphically, they would appear as shown by curve 52 in prior art FIG. 6B, in which brighter pixels have greater pixel values. The location of the endocardium is not the peak of the curve 52, which is in the vicinity of the center of the heart wall, but relates to the sense of the slope of the curve. The slope of the curve 52 is therefore analyzed by computing the differential of the curve 52 as shown by the curve 58 in prior art FIG. 6C. This differential curve has a peak 56, which is the maximal negative slope at the outside of the heart wall (the epicardium). The peak 54, which is the first major peak encountered when proceeding from right to left along curve 58, is the maximal positive slope, which is the approximate location of the endocardium. The pixels along and parallel to line 48 in FIG. 6A are analyzed in this manner to find the endocardial wall and hence the location of the endocardial apex, marked by the small box 46 in prior art FIG. 5.

While the Philips ABD inventions do provide a tool for drawing cardiac borders, such prior art systems and processes cannot always be relied upon to identify true endocardial borders. For example, in ultrasound imaging which includes the use of contrast agents, signal energy returning from the contrast agent (reflecting, resonating or bursting microbubbles) is not always homogeneous. That is, returning signals are affected by ultrasound speckle, blood supply, non-uniform bubble destruction, signal attenuation along scanlines, etc. Further, due to speckle, signal loss and variation in the myocardium, applying a simple thresholding technique to the myocardium edge yields only staggered points, which may or may not be linear. Results include borders drawn with edge points that do not fill along the border at all.

It is therefore at least one object of the present invention to provide a method for endocardial and epicardial delineation of the myocardium for use with parametric imaging of cardiac perfusion, and ultrasound system for implementing same.

It is at least another object of the invention to provide a method for endocardial and epicardial delineation of the myocardium for use with parametric imaging of the cardiac perfusion, which utilizes an array of thresholds corresponding to image depth, and ultrasound system for implementing same. Preferably, the imaging depth is determined as a function of a center scanline in an ultrasound cardiac image.

It is at least another object of the invention to provide a method by which endocardial, epicardial and apical edges of the myocardium are approximated by smooth curves, and ultrasound system implementing same. Preferably, the inventions use a maximization function to realize the best fit of threshold-determined points of a polynomial function of degree N, where N is an integer number.

And it is at least another object of the invention to provide an ultrasound imaging method and diagnostic imaging system which shows improved tissue boundary delineation over those methods and system known in the conventional arts, with or without the use of ultrasound contrast agents.

The following drawings are included to provide the reader with a basic understanding of the invention.

Those skilled in the art should note that while a substantial portion of the disclosure refers particularly to cardiac and contrast-enhanced ultrasound imaging and diagnostics, reference thereto is for exemplary purposes only. The present invention is directed to an improved method for delineating tissue boundaries in general, through the use of the inventive thresholding technique described, and is not limited to cardiac imaging and diagnostics, or other vascular-related imaging and diagnostics.

More particularly, while the prior art for automatic border detection does provide tools for drawing tissue borders, such conventional border detection and delineation systems and processes cannot always be relied upon to identify true tissue borders. This is sometimes the case with Philips ABD inventions as discussed above. More particularly, visual distinction between pixels is at times unclear while using the Philips ABD inventions for a variety of reasons. For example, in contrast agent enhanced ultrasound imaging, signal energy returning from the contrast agent (reflecting, resonating or bursting microbubbles) is not always homogeneous. That is, returning signals are affected by ultrasound speckle, tissue inhomogeneity, blood supply, non-uniform bubble destruction, signal attenuation along scanlines, etc. Further, due to speckle, signal loss and variation in the myocardium, applying a simple thresholding technique to the myocardium edge yields only staggered points, which may or may not be linear. Results include borders drawn with edge points that do not fill along the border at all.

In a preferred embodiment, the present invention overcomes the shortcomings of the conventional arts by generating and utilizing an array of thresholds which are a function of image depth. The array of thresholds is then used to identify endocardial and epicardial borders more accurately than known ABD or ACD methods. That is, once the threshold array is acquired and stored, the orientation of the structure (e.g., heart) with respect to the direction of a center scanline is determined. The center scanline is defined by first automatically (or manually) identifying several landmarks or key points within the image, and using the landmarks to generate center the scanline. Preferably, three (3) key points or landmarks are used. Accurate thresholds are then calculated from the array of thresholds for use at a given depth to combat signal loss or attenuation at the depth when searching for structural edges.

Figure 7:
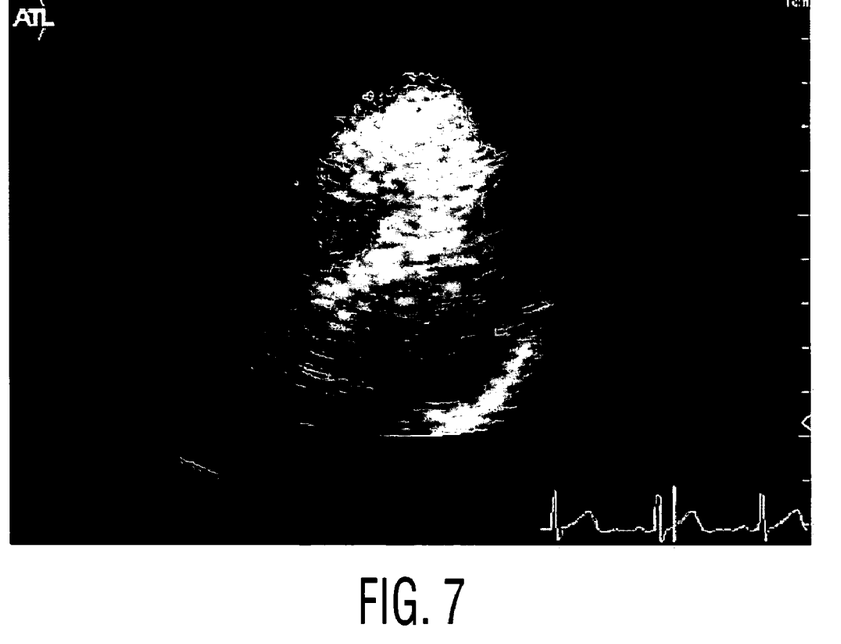
FIG. 7 is a cardiac image showing swirls of a contrast agent in the LV and a gradual loss of contrast signal toward the mitral level.
Figure 8:
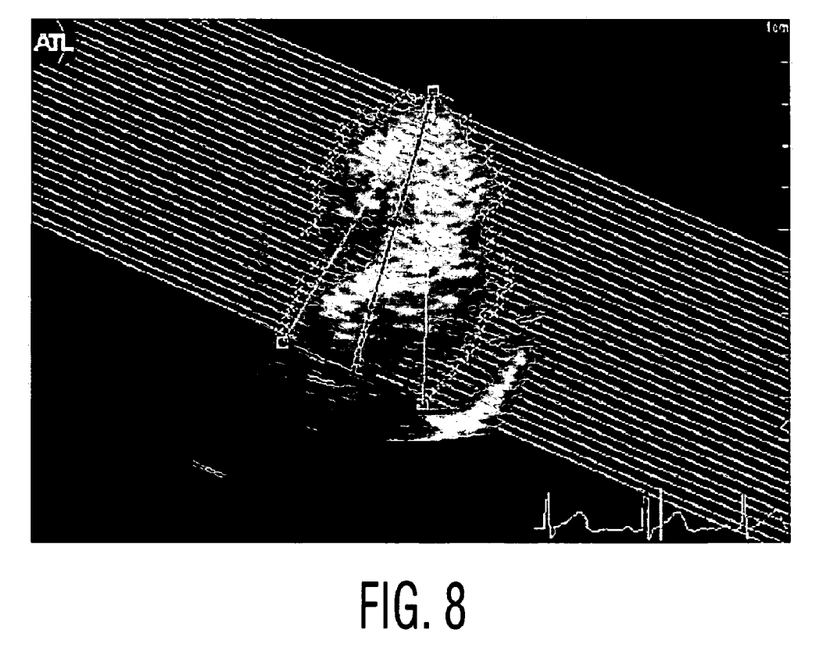
FIG. 8 is a cardiac image showing three key points defining the mitral plane and apex of the LV cavity as provided automatically by the present invention.

In one implementation, the embodiment may be utilized in cardiac diagnostic imaging. That is, FIG. 7 herein shows a high quality cardiac image with contrast agent in the left ventricular (LV) cavity. While the distinction between the LV cavity and myocardium is generally clear in this figure, swirls may be seen in the LV. A gradual loss of contrast signal toward the mitral level is seen as well, which may at times thwart simple threshold based segmentation. FIG. 8 shows three key points or landmarks already mentioned. The three key points or landmarks may be automatically determined, as described in the Philips prior art ABD inventions, or may be manually input by a user. The three points are shown as white squares in FIG. 8, and define the mitral valve (MMA and LMA) and apex of the LV cavity. A central axis or scanline is drawn between the apical point of the LV cavity and the bisector point of the mitral plane (seen as a vertical scanline in the figure).

The reader should note that the key points or landmarks (e.g., 3) described are identified in particular merely for exemplary purposes. The invention is not limited to these particular three points or even a fixed number of key points. That is, as long as one skilled in the art is able to determine a set of thresholding values which are defined and correlated as a function of image depth and/or quality, any method may be used for defining a point of axis within the image for use as a focal point or landmark. It is the use of the thresholding values which renders the invention unique. Moreover, while the inventions are described in the preferred embodiments for use in cardiac ultrasonic imaging, they are not limited to tissue border detection and delineation within the heart only. The principles set forth herein may be implemented in any ultrasonic imaging process which attempts to delineate tissue boundaries in any organ or vessel, particularly in processes using contrast agents, for example, any perfusion analysis, and for 3-D imaging.

For that matter, the inventions described herein are not limited to two-dimensional planar ultrasound echo images, but may 3-D contrast-enhanced images of the heart or other organs. In 3-D applications, key landmarks and chord projections are extended to the three-dimensional space, and a 3D-contour model is used rather than a polygon approximation the 3-D boundaries of the structure.

The method includes calculating a series of chords in such a manner that the chords project out from the central axis toward the myocardium. In one implementation, the chords may be represented by gray lines in the cardiac image as shown in FIG. 8. The chords therein are arranged to be parallel to the mitral valve plane, and spaced at regular intervals. At the origin of each chord (intersection of gray parallel lines and the central scanline at the central axis), small neighborhoods of pixel intensity values are summed, and the mean of the value is determined by the disclosed method. This is one process for defining a threshold for use herein, where the threshold value is a percentage of the mean value found for each chord. Traveling along a particular chord, starting from the central axis, if the intensity value is determined to fall below the threshold for N consecutive pixels, the area is determined to be an edge (marked by white "X's" in FIG. 8). The method requires repetition of this step in the process for all chords. Because a new threshold is determined for each chord, the process adapts to the local intensity when trying to determine edges.

The present invention also addresses other shortcomings in the art. That is, due to speckle, signal loss, and variation (for example, in the left ventricle and myocardium) applying a simple threshold at the edges of a tissue structure (e.g., the myocardium) yields a series of staggered points. The may be readily seen in FIG. 9 along the edges of the myocardial border. And because prior art thresholding techniques do not consider image morphology, many points do not fall along the actual border at all. To remedy this, the invention provides smooth curves to approximate the edges of a tissue structure being imaged, for example, the endocardial, epicardial and apical edges of the myocardium. The invention does so by fitting the threshold-determined points with a polynomial function of degree N (where N is an integer number), realizing a robust and visually pleasing edge. The inventive approach requires three distinct steps to realize a smooth curve which accurately approximates the tissue edges. The first step requires that a polynomial of degree N be fit through all of the threshold-determined points of a particular edge, for example, left endocardial. The second step requires calculating the mean distance between the polynomial fit and actual threshold-determined points. The third step requires eliminating outlier points which are further than a factor F times (F is an integer value) the mean distance. These second and third steps are iterated until no additional outlying points are illuminated. The result is a robust curve fitting. The result, however, does not provide any information about how well the polynomial fits the actual border.

Figure 9:
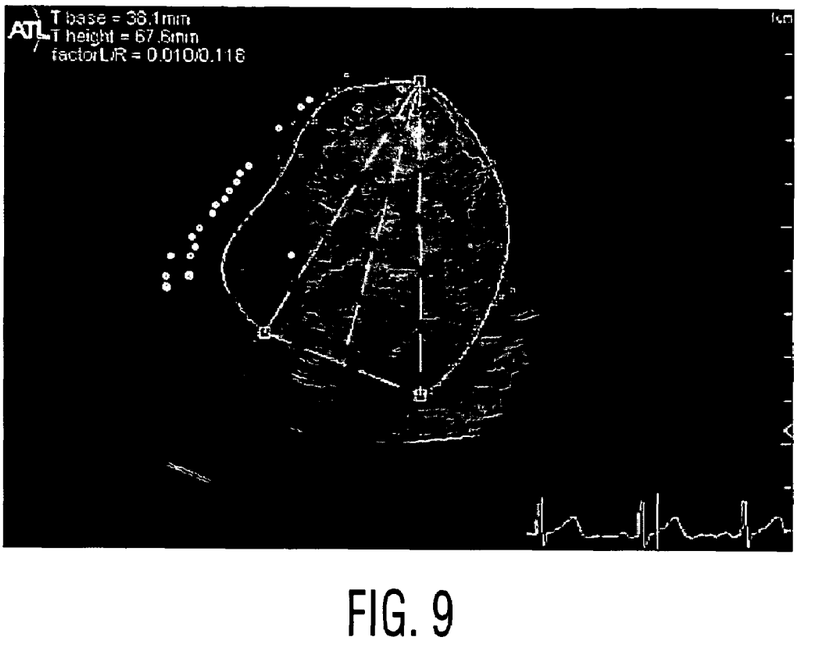
FIG. 9 is a cardiac image highlighting the inventive polynomial fitting of this invention to a series of threshold determined points.

The invention further provides for determining the best polynomial approximation to the real edges through the use of a maximization function. The required maximization function uses three parameters. The three parameters are the mean intensity along the polynomial, the number of threshold points used to approximate the polynomial and goodness-of-fit parameter (such as the chi-squared error) of the polynomial approximation to the threshold points. FIG. 9 is a cardiac image which shows the inventive polynomial fitting to a series of threshold-determined points which are very far from the scanline or center axis described above. Many of the threshold points, seen as small white x's in FIG. 9, are determined by the inventive process to be outliers. The invention delineates these outliers in the image by marking them as small white filled circles (see FIG. 9). These are marked as filled circles merely to distinguish them from x's because the outliers fall outside the echo sector.

Figure 12:
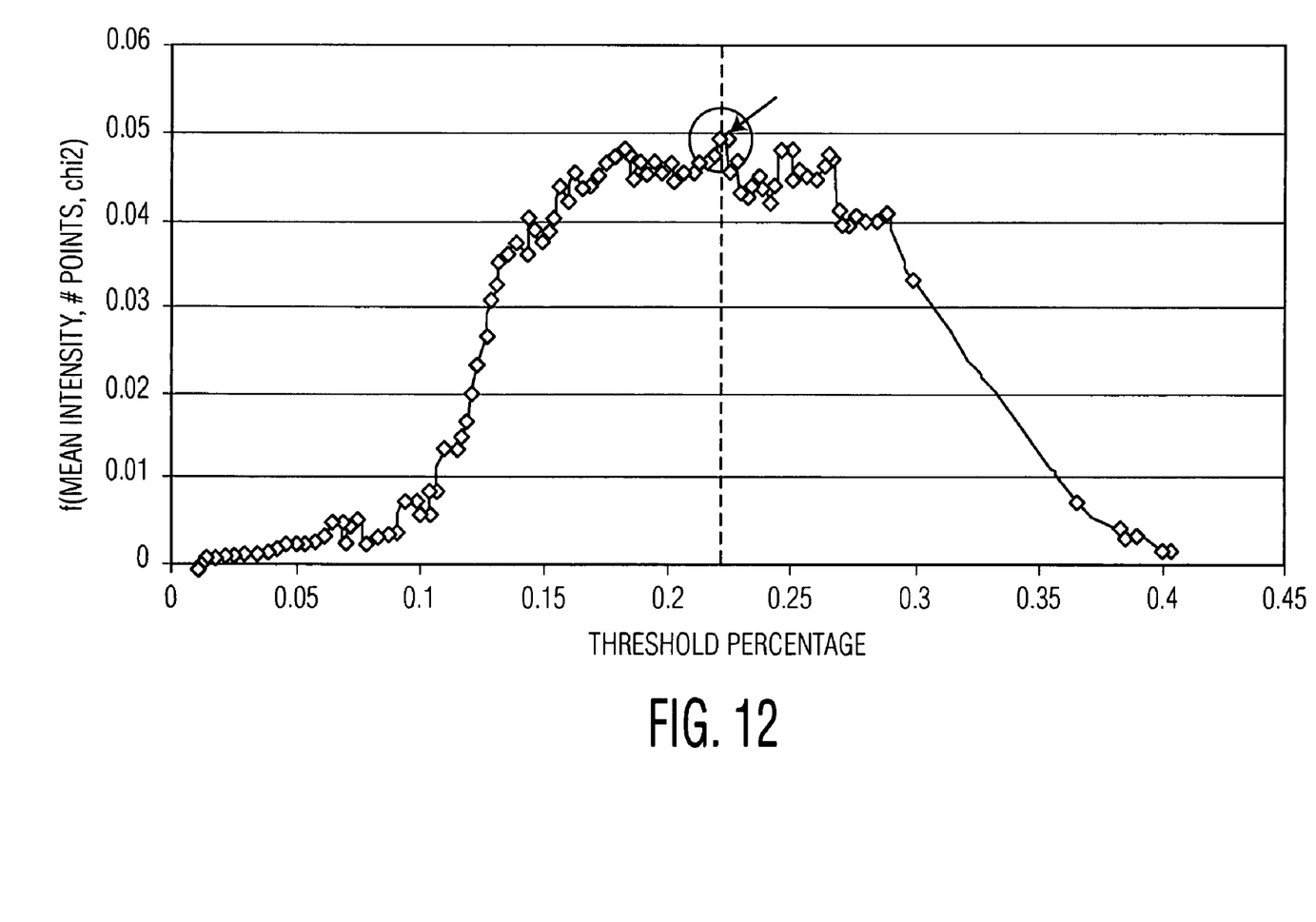
FIG. 12 is a graph of the maximization function used to determine which threshold percentage yields the best edge.

The method of determining the best polynomial, which uses these three parameters, does so iteratively. The threshold values determined along each chord from the central axis are multiplied by a percentage factor, which varies between an upper and lower limit. The polynomial fit and maximization function are calculated for each threshold percentage, and a graph is generated, as shown in FIG. 12. The process is iterated so that one polynomial fit and one maximization function result is generated for each arbitrary step between the upper and lower threshold limits. The maximization function attempts to simultaneously minimize the mean intensity along the polynomial approximation, maximize the number of points used in the polynomial approximation, and minimize the error between the edge points and the polynomial approximation (minimize the chi-squared error). The output of maximization function is graphed per iteration, and a peak in the graph indicates the best polynomial fit at the best threshold (arrow in FIG. 12). Results have shown that such an approach yields maximized polynomial approximation to the real edge in terms of position and border type.

Figure 10:
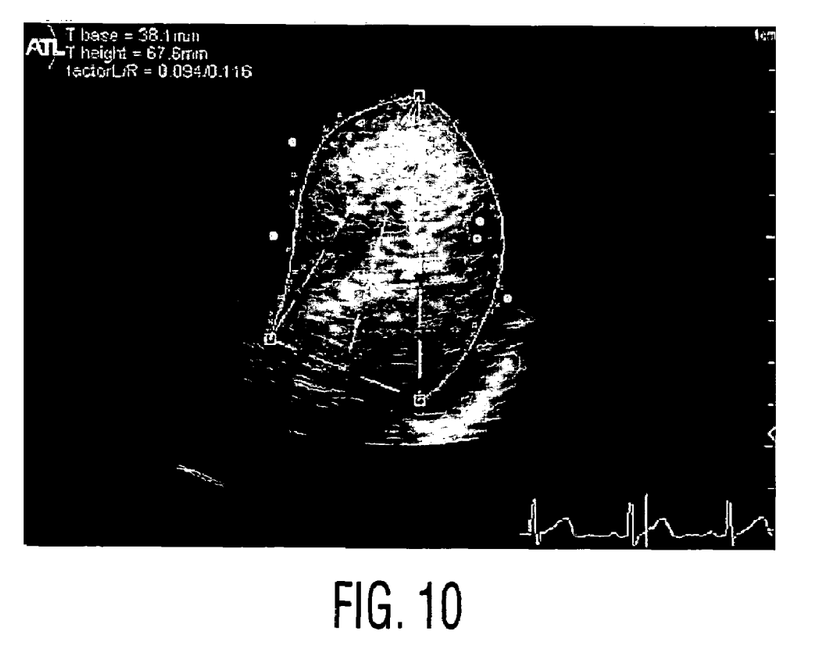
FIG. 10 is a cardiac image representing iteration of the polynomial fitting of this invention (relative the FIG. 8 image)

FIG. 10 shows a further iteration of the polynomial fitting process with respect to the image, and its state as shown in FIG. 9. There, the threshold percentage is increased, and the maximization function has achieved a higher value than that which was achieved in the iteration shown in FIG. 9. That is, more points, highlighted by the white x's in the figure, are used for the curve fitting, and the number of outliers (small white filled circles) is significantly decreased. This proves to be a very convenient tool in any tissue border delineation operation, rendering subsequent volume measurements quite routine.

Figure 11:
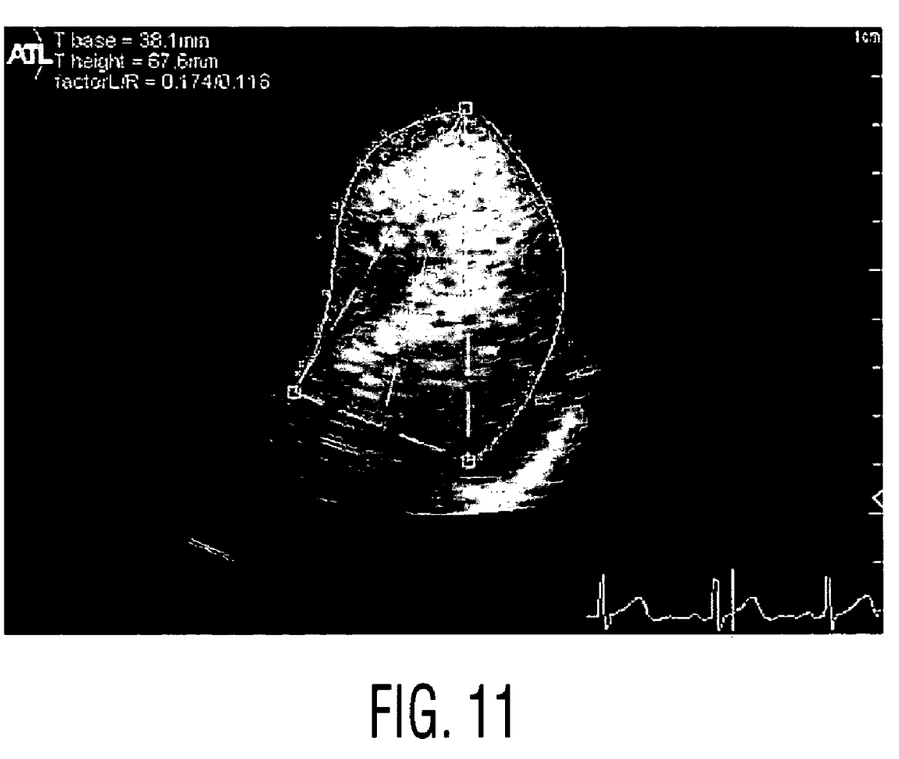
FIG. 11 is a cardiac image highlighting an ability of the invention to provide a best estimate of a true edge or tissue boundary.

FIG. 11 shows a representation of the FIG. 9 image as the best estimate of the true edge by the inventive process of this invention. The number of points used in the polynomial curve fitting has been maximized, and the mean intensity of the threshold points along the edges has been minimized. Moreover, the chi-squared error between the polynomial approximation and the threshold point is minimized. More to the point, the results of the inventive maximization function are graphically shown in FIG. 12, where the x-axis is the iteration number, with each iteration corresponding to particular threshold percentage, and the y-axis is the value of the maximization function. The peak, as indicated by the arrow in FIG. 12, corresponds to threshold percentage values, which, in turn, yield the best approximation of the edge.

Figure 13:
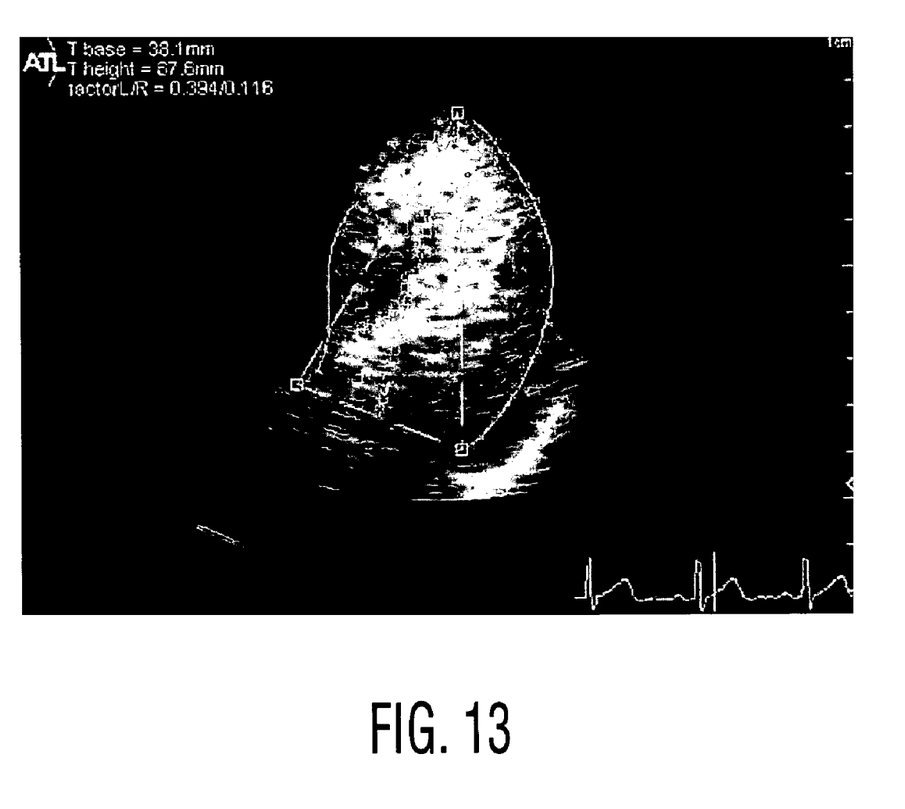
FIG. 13 is a cardiac image highlighting another iteration of the cardiac image as first seen in FIG. 9.

FIG. 13 shows another iteration of the cardiac image as first seen in FIG. 9, where the threshold percentage is too high. The threshold points remain in the left ventricular cavity and the maximization function yields very low values, as can be seen by the right side of the graph in FIG. 12. The trace is fit to the threshold values, marked by the x's in the figures. The trace is fit using a polynomial approximation of degree N, preferably of degree 2, 3, or 4. The higher the degree of the polynomial approximation, the more freedom for curviness for the approximation. The reader should note that it is along the center scanline that the initial estimates of the threshold are made, and that the landmarks are merely setup to create a frame of reference for the final curve fit. The key points or landmarks also set up a "known" geometry that passes through the middle of the object whose edges we want to identify, and create known endpoints for the final curve fit. As mentioned above, while three key points or landmarks are preferred, varying circumstances might require more or less than three key points.

The inventive process described herein can be automated, such that all of the steps described occur with a minimum of user interaction, or may be used interactively, with the clinician to adjust threshold percentage limits to realize optimal tissue border definition, and the increased accuracy of any volumetric quantification occurring subsequently based thereon. The reader should note that the preferred embodiments of the invention as set forth herein are is for exemplary purposes only. The scope of the invention is limited only by the scope and limitations of the claims appended hereto.

The invention claimed is:

1. A method of defining a tissue border in a medical ultrasound image, comprising: acquiring a 2-D planar ultrasound image; identifying at least one key point or landmark within the ultrasound image; locating and identifying a center scanline in the ultrasound image relative the key point or benchmark; determining an array of threshold values correlated to the center scanline as a function of image depth; filling a trace to a tissue border related to the center scanline and the array of threshold values; and displaying an ultrasonic image with a fitted trace displayed at the tissue border.

2. The method of claim 1, wherein the step of locating comprises matching a geometric template corresponding to the geometric relationship of the at least one key point or benchmark in the ultrasound image to the scanline.

3. The method of claim 1, wherein the step of identifying includes that the at least one key point or benchmark is input automatically.

4. The method of claim 1, wherein the step of identifying includes that the at least one key point or benchmark is input by a user.

5. The method of claim 1, wherein the step of identifying includes that the number of key points or benchmarks is three.

6. The method of claim 1, wherein the medical ultrasound images may be three-dimensional (3-D).

7. The method of claim 1. wherein the step of identifying includes identifying the mitral valve in the image, and the step of fitting includes determining a series of chords out from the scanline to the tissue border, which chords are parallel to the mitral valve plane and occur at regular intervals.

8. The method of claim 7, wherein at the origin of each chord, small neighborhoods of pixel intensity values are summed, and a mean is determined for each chord.

9. The method of claim 8, wherein a threshold value is determined for each chord as a percentage of the mean value found for each chord.

10. The method of claim 7, wherein the medical ultrasound image is contrast agent-enhanced.

11. The method of claim 7, further including a step of evaluating each pixel value of a particular chord, beginning with the chord pixel value at the center scanline, and if the intensity value for each pixel value is found to be below the threshold for N consecutive pixels, qualifying an area comprising the N values as an edge.

12. The method of claim 11, wherein the step of evaluating requires that a polynomial of degree N be fit through all of the threshold-determined points of a particular edge, calculating a mean distance between the polynomial fit and actual threshold-determined points and eliminating outlier points which are further than a factor F times the mean distance.

13. The method of claim 12, further including a step for determining the best polynomial approximation to the real edges through the use of a maximization function.

14. The method of claim 12, wherein the maximization function uses the mean intensity along the polynomial, the number of threshold points used to approximate the polynomial and the chi-squared error of the polynomial approximation to the threshold points.

15. The method of claim 14 where the chi-squared approximation may be substituted for an arbitrary "goodness-of-fit" estimate.

16. The method of claim 14 where the maximization function can contain any number of parameters.

17. The method of claim 1, wherein the ultrasound image is a cardiac image and the three key points define the mitral valve and apex of the LV cavity.

18. The method of claim 17, wherein the tissue border is the border of a surface of the heart.

19. The method of claim 17, wherein the border is the endocardium of the heart.

20. The method of claim 1, wherein the ultrasonic image comprises an image of a chamber of the heart which includes an apex; and wherein the step of locating comprises: defining a first line along a portion of the septal wall of the heart chamber proximate to the apex; defining a second line along a portion of the lateral wall of the heart chamber proximate to the apex; and bisecting the angle between the first and second lines to locate the apex.

21. The method of claim 20, further comprising a step of analyzing the pixel intensity along the bisected angle to locate the apex of the heart chamber.

22. The method of claim 21, wherein the heart chamber is the left ventricle.

23. A method of defining a tissue border in a medical ultrasound image, comprising: acquiring a 3-D ultrasound volumetric image; identifying at least three key points or landmarks within the 3-D volumetric image; locating and identifying a center scanline in the ultrasound image relative the three key points or landmarks; determining an array of threshold values correlated to the center scan line as a function of image depth; fitting a trace to a tissue border related to the center scanline and the array of threshold values; and displaying an ultrasonic image with a fitted trace displayed on the tissue border.

24. The method of claim 23, wherein the step of locating comprises matching a geometric template corresponding to the geometric relationship of the at least the key points or landmarks in the ultrasound image to the scanline.

25. The method of claim 23, wherein the at least three key points or landmarks are input automatically.

26. The method of claim 23, wherein the at least three key points or landmarks are input by a user.

27. The method of claim 23, wherein the step of fitting includes determining a series of chord projections out from the scanline to the myocardium, which chord projections are parallel and occur at regular intervals.

28. The method of claim 27, further including a step of evaluating each pixel value of a particular chord projection, beginning with the chord pixel value at the center scanline, and if the intensity value is below the threshold for N consecutive pixels, qualifying an area comprising the N values as an edge.

29. The method of claim 28, wherein at a fixed distance from the origin of each chord projection, small neighborhoods of pixel intensity values are summed and a mean value is determined.

30. The method of claim 29, wherein a threshold is determined as a percentage of the mean value found for each chord projection.

31. The method of claim 28, wherein the step of evaluating requires that a contour model of degree N be fit through all of the threshold-determined points of a particular edge, calculating a mean distance between a set of points defining the contour model and actual threshold-determined points and eliminating outlier points which further than a factor F times the mean distance.

32. The method of claim 31, further including a step for determining the best polynomial approximation to the real edges through the use of a maximization function.

33. The method of claim 32, wherein the maximization function uses the mean intensity along the contour model, the number of threshold points used to approximate the contour model and the chi-squared error of the polynomial approximation to the threshold points.

34. The method of claim 33 where the chi-squared approximation may be substituted for an arbitrary "goodness-of-fit" estimate.

35. The method of claim 33 where the maximization function can contain any number of parameters.

36. The method of claim 23, wherein the ultrasound image is a cardiac image and the three key points define the mitral valve and apex of the LV cavity.

37. The method of claim 36, wherein the border is the endocardium of the heart.

38. The method of claim 36, wherein the border is the epicardium of the heart.

39. The method of claim 23, wherein the ultrasonic image comprises an image of a chamber of the heart which includes an apex, and wherein locating comprises: defining a first line along a portion of the septal wall of the heart chamber proximate to the apex; defining a second line along a portion of the lateral wall of the heart chamber proximate to the apex; and bisecting the angle between the first and second lines to locate the apex.

40. The method of claim 39, further comprising analyzing the pixel intensity along the bisected angle to locate the apex of the heart chamber.

* * * * *